(12) United States Patent
Boe

(10) Patent No.: US 9,662,274 B2
(45) Date of Patent: May 30, 2017

(54) METHOD OF ORALLY ADMINISTERING A TREATING AGENT OVER AN EXTENDED PERIOD

(71) Applicant: Irwin N. Boe, Leawood, KS (US)

(72) Inventor: Irwin N. Boe, Leawood, KS (US)

(73) Assignee: INNOVATIVE PRODUCTS, INC., Leawood, KS (US)

( * ) Notice: Subject to any disclaimer, the term of this patent is extended or adjusted under 35 U.S.C. 154(b) by 435 days.

(21) Appl. No.: 14/250,384

(22) Filed: Apr. 11, 2014

(65) Prior Publication Data

US 2015/0290122 A1    Oct. 15, 2015

(51) Int. Cl.
| | |
|---|---|
| *A61C 3/02* | (2006.01) |
| *A61C 5/00* | (2006.01) |
| *A61J 7/00* | (2006.01) |
| *A61C 7/00* | (2006.01) |
| *A61K 9/00* | (2006.01) |
| *A61C 19/06* | (2006.01) |

(52) U.S. Cl.
CPC ............... *A61J 7/0092* (2013.01); *A61C 7/00* (2013.01); *A61C 19/063* (2013.01); *A61K 9/0063* (2013.01)

(58) Field of Classification Search
CPC .. A61C 7/00; A61C 5/04; A61C 19/06; A61C 19/063; A61C 19/066; A61J 7/0092; A61K 9/006; A61K 9/0063; A61K 9/0053; A61K 9/0056
USPC ........ 433/215, 217.1, 88–90, 229, 24, 80, 6; 424/435, 49–59; 514/900–902; 1/8, 81, 1/87

See application file for complete search history.

(56) References Cited

U.S. PATENT DOCUMENTS

| | | | | |
|---|---|---|---|---|
| 3,503,127 A | * | 3/1970 | Kasdin | A61C 13/24 433/199.1 |
| 3,600,807 A | * | 8/1971 | Sipos | A61C 19/06 433/167 |
| 3,754,332 A | * | 8/1973 | Warren, Jr. | A61C 15/00 132/321 |
| 4,175,326 A | * | 11/1979 | Goodson | A61K 9/0063 424/435 |
| 4,484,895 A | * | 11/1984 | Smiley | A61C 7/006 433/18 |
| 4,676,752 A | * | 6/1987 | Lefkowitz | A61J 7/0092 433/229 |
| 4,741,700 A | * | 5/1988 | Barabe | A61C 5/00 433/215 |
| 4,892,483 A | * | 1/1990 | Douglas, Jr. | A61J 7/0092 433/215 |
| 4,959,052 A | * | 9/1990 | Cox | A61C 5/08 433/218 |
| 5,049,077 A | * | 9/1991 | Goldin | A61J 7/0092 433/229 |
| 5,074,786 A | * | 12/1991 | Woodward | A61J 7/0092 433/229 |

(Continued)

*Primary Examiner* — Loan H Thanh
*Assistant Examiner* — Garrett Atkinson
(74) *Attorney, Agent, or Firm* — Erickson Kernell IP, LLC

(57) ABSTRACT

An implantation device for and method of orally administering a time released treating agent to a user over an extended period, including fixedly engaging at least one tooth of the user with the agent, and releasing the agent within the oral cavity, so as to be locally or systemically delivered to a remainder portion of the user separate from the teeth over the period.

15 Claims, 4 Drawing Sheets

(56) References Cited

U.S. PATENT DOCUMENTS

| | | | | |
|---|---|---|---|---|
| 5,194,003 A * | 3/1993 | Garay | A61J 7/0092 | 433/215 |
| 5,599,553 A * | 2/1997 | Chung | A61K 9/0063 | 424/435 |
| 6,193,994 B1 * | 2/2001 | Lee | A61K 9/0063 | 424/426 |
| 6,790,035 B2 * | 9/2004 | Tricca | A61C 7/00 | 264/19 |
| 7,192,966 B2 * | 3/2007 | Mayo-Alvarez | A61K 31/137 | 424/55 |
| 7,648,360 B2 * | 1/2010 | Kuo | A61C 7/08 | 206/63.5 |
| 7,878,801 B2 * | 2/2011 | Abolfathi | A61C 7/00 | 433/6 |
| D641,478 S * | 7/2011 | Belvedere | D24/180 | |
| 8,067,046 B2 * | 11/2011 | Schleef | A24B 13/00 | 131/111 |
| 8,501,222 B2 * | 8/2013 | Mythen | A61B 17/244 | 424/440 |
| 8,899,976 B2 * | 12/2014 | Chen | A61C 7/00 | 433/6 |
| 2002/0081546 A1 * | 6/2002 | Tricca | A61C 7/00 | 433/6 |
| 2002/0106407 A1 * | 8/2002 | Coleman | A61K 31/135 | 424/468 |
| 2003/0138757 A1 * | 7/2003 | Cohen | A61C 5/00 | 433/217.1 |
| 2005/0180930 A1 * | 8/2005 | Abiru | A61K 8/738 | 424/58 |
| 2010/0233257 A1 * | 9/2010 | Herry | A61K 9/0056 | 424/464 |
| 2011/0117175 A1 * | 5/2011 | Rosenbaum | A61K 9/006 | 424/443 |
| 2011/0200972 A1 * | 8/2011 | Mythen | A61B 17/244 | 433/217.1 |

* cited by examiner

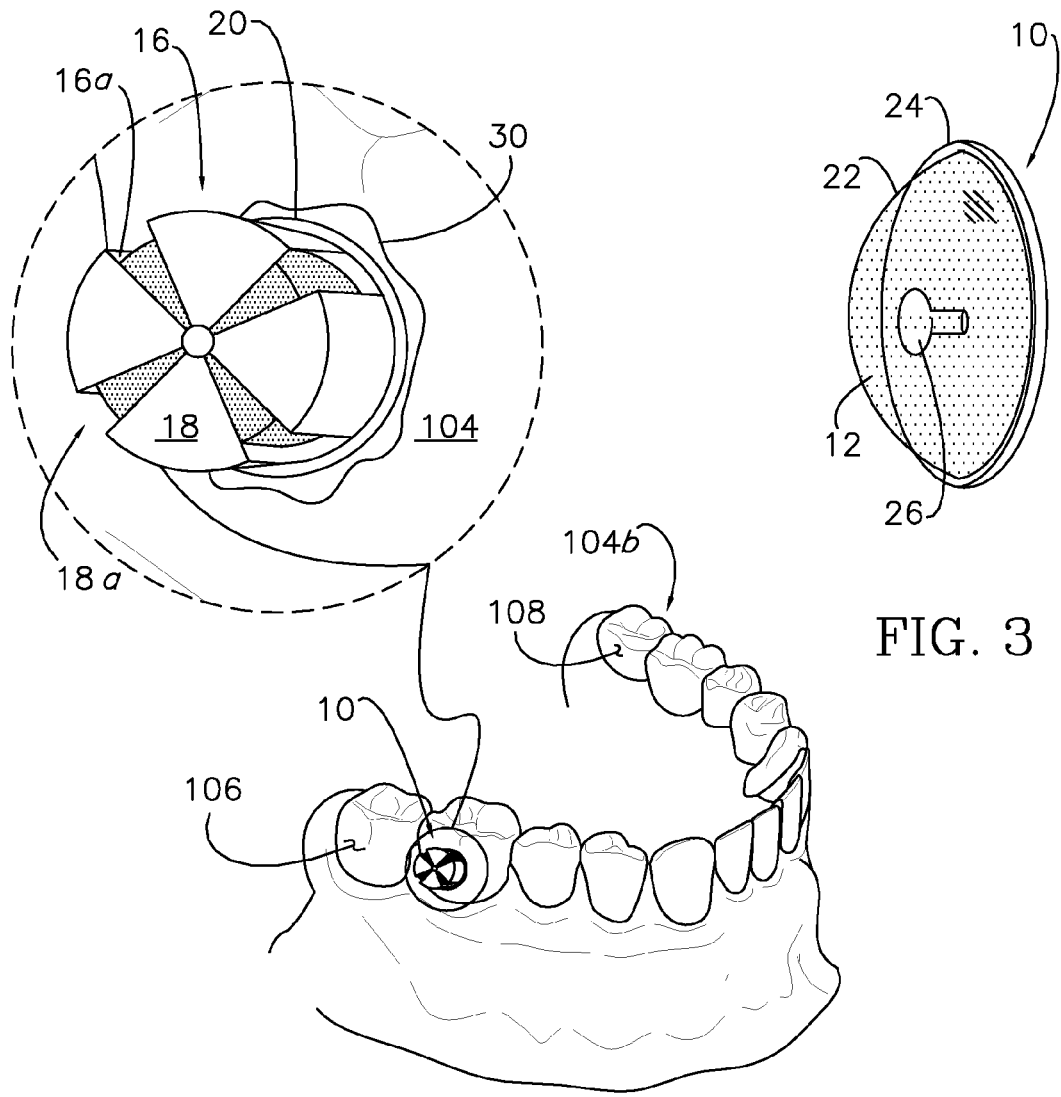
FIG. 3
FIG. 2
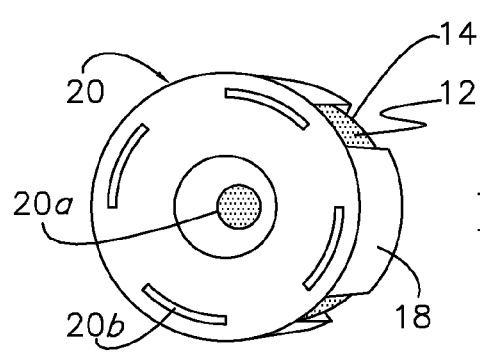
FIG. 2a

METHOD OF ORALLY ADMINISTERING A TREATING AGENT OVER AN EXTENDED PERIOD

BACKGROUND OF THE INVENTION

1. Field of the Invention

The present disclosure generally relates to methods of orally administering a treating agent to a user, and more particularly, to methods of administering such agents, which include fixing the agent relative to at least one tooth and releasing the agent within the oral cavity over an extended period.

2. Discussion of Prior Art

Providing efficient and efficacious means for administering a treating agent (i.e., any substance, molecule, element, compound or otherwise active ingredient operable to effect an intended benefit) to a user over an extended period remains a vital societal concern. For example, in the medical and dental arts, doctors commonly prescribe treating agents, such as drugs and medicants, to patients for repetitive oral consumption. It is widely appreciated, however, that repetitive oral consumption presents various concerns. Foremost, where self-administered, users, such as the elderly and mentally infirm, often forget or unintentionally fail to adhere to the specified regiment and schedule. This may render the treatment ineffective and in some cases worsen the mal condition. Where manual administration is difficult, as with swallowing large pills/capsules, it is further appreciated that many users become deterred from taking the prescribed agent all together. Further, even where oral consumption is properly performed, inefficiencies, such as the "first pass effect"—the percentage of drug lost to metabolization in the liver, often result in increased costs, waste, and in some cases harmful side effects. Lastly, it is appreciated that similar human error concerns exist for extended intravenous, and other forms of administration.

BRIEF SUMMARY OF THE INVENTION

The present invention addresses these and other concerns, and presents an implantation device for and method of orally administering a treating agent, such as a drug, therapeutic agent, medicant, or aromatic/flavor producing agent, to a user. In general, the method includes fixing the agent relative to at least one tooth, releasing the agent over the period within the cavity, and delivering the agent to a remainder portion of the user separate from the teeth, as a result of releasing the agent over the period.

As such, the invention is useful for administering the agent autonomously, which removes the ability of the user to forget, err, or be deterred, and enables delivery even when repetitive oral consumption is impractical or impossible (e.g., while sleeping, etc.). By releasing the agent within the oral cavity, the invention enables sustained administration through the mucous membrane lining or mucosa, which offers several advantages. For instance, it is appreciated that the oral mucosal route provides direct access to the bloodstream without having to travel through the gastrointestinal tract, which allows the drug to avoid the "first pass effect". As a result, drug delivery across the oral mucosa potentially offers patients more rapid onset of action at a lower dosage. The invention offers healthcare providers a means to provide more accurate and targeted drug delivery. With particular relevance to dental patients, the invention is further useful for locally treating gum decease or ailment over a sustained period. Finally, where an aromatic/flavor producing agent is employed, the invention is yet further useful for offering the user long lasting enjoyment and comfort. Thus, the invention offers a delivery means that is more reliable, convenient, and in some cases efficient and efficacious, when compared to prior art methods of oral administration.

The disclosure, including a variety of implantation devices, agents, and compounds suitable for use herein, may be understood more readily by reference to the following detailed description of the various features of the disclosure and the examples included therein.

BRIEF DESCRIPTION OF THE SEVERAL VIEWS OF THE DRAWING

A preferred embodiment(s) of the invention is described in detail below with reference to the attached drawing figures of exemplary scale, wherein:

FIG. 2 is a perspective view of a lower set of teeth, and in enlarged caption view, a button-type implantation device defining an interior space and attached to the exterior lateral surface of a back molar, in accordance with a preferred embodiment of the invention;

FIG. 2a is a perspective view of the back of the device shown in FIG. 2;

FIG. 3 is an enlarged perspective view of a button-type implantation device comprising a coat formed at least in part by the agent, and a base plate having an attachment prong extending from the plate, in accordance with a preferred embodiment of the invention;

DETAILED DESCRIPTION OF THE INVENTION

Figure 1:
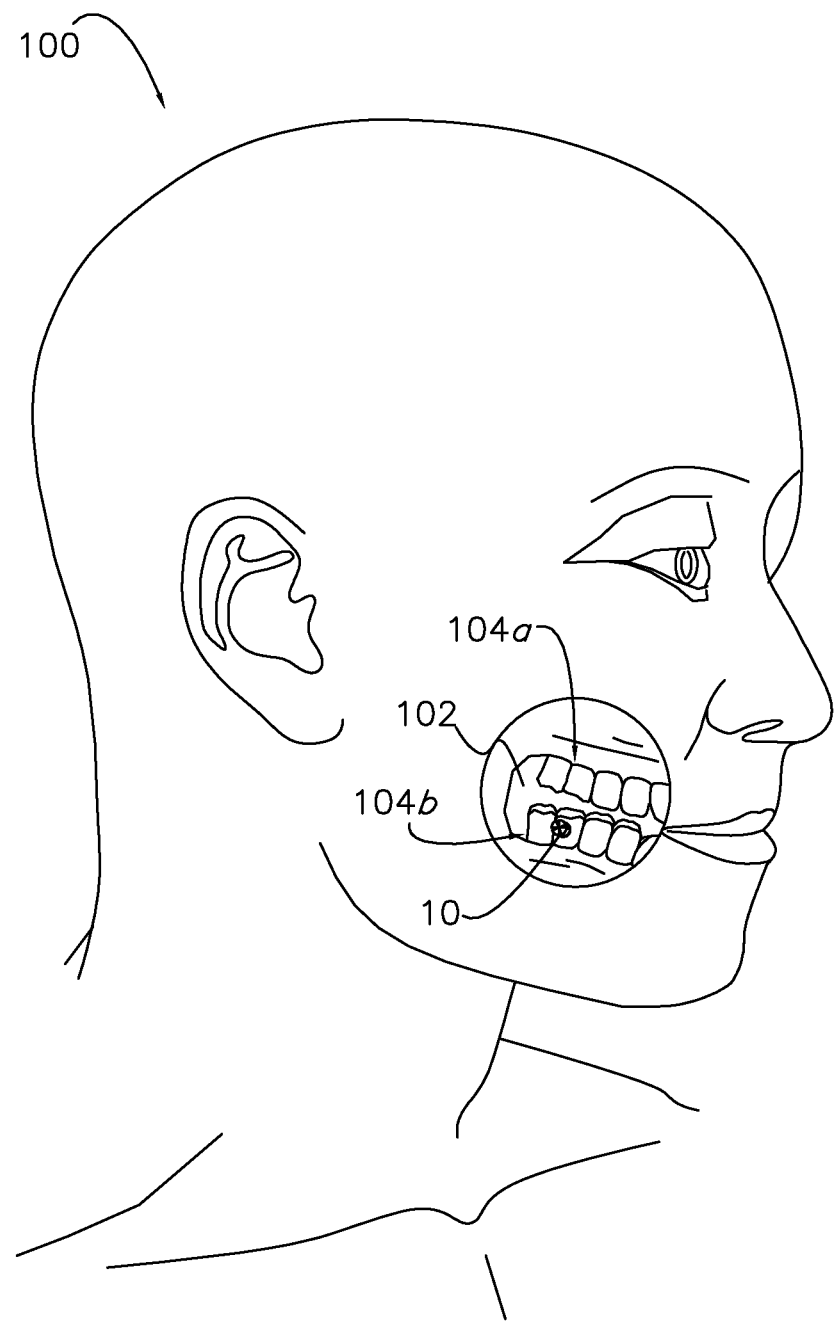
FIG. 1 is a perspective view of a human user, particularly illustrating an oral cavity defined and plurality of teeth presented thereby, and further illustrating an implantation device fixedly bonded to a lower molar, in accordance with a preferred embodiment of the invention.

The following description of the preferred embodiments is merely exemplary in nature and is in no way intended to limit the invention, its application, or uses. The invention generally presents an implantation device 10 for and method of orally administering a treating agent 12 to a user 100 over an extended period. The invention is described and illustrated herein with respect to a human user 100 (FIG. 1) that defines an oral cavity 102 and presents at least one, and more preferably, a plurality of teeth 104; however, it is well appreciated by those of ordinary skill in the art that minor modification may be made, for example, to the size and/or chemical composition of the device 10, to facilitate use by an animal user that bear teeth or similar structure within an oral cavity, without departing from the invention. The engaged teeth 104 need not be indigenous to the user 100, and may be presented by dentures or other false constructions.

In operation, the inventive device 10 is affixed relative to either one of upper or lower sets of fixed teeth 104a,b. The device 10 stays in place autonomously, as opposed to being held in place by clenching the sets 104a,b, which distinguishes the invention from trays, mouthpieces, and the like. In a preferred embodiment, the device 10 in any form functions to deliver the agent 12 to a remainder portion of the user 100 separate from the teeth 104, and more preferably, separate from the mouth, so as to be further distinguishable from whitening strips, and the like, which deliver an agent directly to the teeth. That is to say, in this embodiment, the teeth 104 of the user 100 are not treated and are used solely as an accessible base to deliver the treating agent 12 to the user otherwise. In another embodiment, the invention recites a novel structure operable to deliver the agent 12 to the teeth 104 over the period, wherein exemplary structural configurations are further discussed below.

Necessarily, it is appreciated that the bond or holding strength between the device 10 and engaged tooth 104 is such that the device 10 does not dislodge under stresses caused during normal operation of the mouth (e.g., tooth brushing, consumption of food and beverages, speaking, etc.). Moreover, the device 10 is configured such that fluid interaction with anticipatory elements and ingredients commonly introduced within the mouth, including fluoride in toothpaste, does not substantially impact the rate of time release or otherwise alter the device 10.

As shown in FIGS. 1-6, the invention is employed within the oral cavity 102 by affixing the agent 12 relative to at least one tooth 104, and more specifically, by directly or indirectly attaching the device 10 to a lateral surface 106,108 of the teeth 104. By limiting engagement to the lateral surfaces 106,108, the device 100 does not interfere with the normal function of the teeth 104. Further, in most applications, the device 10 is preferably attached to the exterior lateral surface 106, so as to minimize interaction with the tongue. The device 10 is configured such that the agent 12 is time releasable (e.g., gradually, incrementally, etc.) within the cavity 102 over a predetermined extended period preferably not less than one hour, more preferably not less than one day, and most preferably not less than one month, depending upon the application. For example, it is appreciated that relief from temporary mal conditions, such as allergies or headaches, may be accomplished through the gradual release of a suitable agent over a 12 to 24 hour period.

As a result of releasing the agent 12 over the period, the agent 12 is delivered systemically or locally to a remainder portion (e.g., the bloodstream, gums, etc.) of the user 100. Once depleted over the period, the device 10 may be removed and replaced, or refilled in place. As previously stated, an efficient method of delivering a drug or medicant agent 12 to the user 100, is through the mucous membrane lining within the cavity 102. The invention functions to that end by releasing the agent 12, so as to be absorbed across the lining.

As used herein the term "treating agent" shall mean any substance, molecule, element, or otherwise active ingredient operable to effect an intended benefit within the user 100 through physical or chemical engagement therewith. Among other things, the agent 12 may be a therapeutic agent, medicant, drug, aromatic/flavor producing agent, a combination of the above, and/or the like. Exemplary drugs and medicants may further include alkylating, anti-metabolite, analgesic, or anti-anxiety agents. For example, in a dental setting, the agent 12 may present a plurality of minocycline microspheres (e.g., minocycline microspheres HCl) that may be used to fight periodontitis. It is appreciated that the treating agent 12 may be directly applied to the teeth 104. That is to say, in its most simple form, the invention may be performed by adhering or painting the agent 12 directly on the teeth 104.

The treating agent 12 may compose a compound 14 operable to effect additional functionality (e.g., promote curing, control the release of the agent, or modify a cavity condition, so as to facilitate delivery/absorption, etc.). For example, the compound 14 may further include an effervescent couple used to enhance drug penetration/absorption across the buccal (inside cheek), sublingual (under the tongue), and gingival (between the lips and gum) mucosae. The preferred effervescent couple evolves gas by means of a chemical reaction triggered by exposure to saliva in the mouth. For example, a soluble acid source, such as citric acid, may be caused to react with a source of carbon dioxide that is mostly basic, such as an alkaline carbonate or bicarbonate, so as to produce carbon dioxide gas. Alternatively, a pH adjusting substance may be included in the compound 14, as it is appreciated that pH levels can influence the relative concentrations of ionized and un-ionized drug, which in turn, affects the dissolution of the drug in the saliva and absorption across the oral mucosa.

In a preferred embodiment, the agent 12 and/or compound 14 is retained by a carrier 16 intermediately affixed to the tooth 104 and operable to effect the intended time release. As shown in FIG. 2, for example, the implantation device 10 may include a reservoir-type carrier 16, wherein the carrier 16 defines a partially enclosed interior space 16a and is attachable to the exterior lateral surface 106 of a rear molar tooth 104. More particularly, the carrier 16 comprises and the space 16a is defined by a plurality of polymeric planar slats 18 radially emanating from a disk base 20. The base 20 is indiscriminately circular in the illustrated embodiment, and defines an insertion hole 20a for receiving the agent 12. A plurality of radially open sectors 20b may be defined adjacent the perimeter of the base 20 for added access to and from the space 16a (FIG. 2a). The planar slats 18 converge at the apex of the carrier 16 opposite the base 20, and are preferably tapered to facilitate convergence. The agent 12 is disposed (e.g., injected) within the space 16a, so that the carrier 16 encapsulates the agent 12. In their final configuration, the planar slats 18 define intermediate gaps 16a configured to allow fluid seepage to and from the space 16a.

As such, once in place, saliva is allowed to flow into the space 16a and interact with the agent 12, so as to release the agent 12 in a controlled manner. That is to say, the agent 12 may be configured to chemically react with, or be slowly dissolved by saliva at a rate configured to effect the desired time release. For example, the compound 14 may present or the agent 12 may be otherwise retained by hydrolysable bonds that break when exposed to the water content of saliva. To release the agent 12 at a different rate, the constituency of the compound 14 may be changed such that the bonds become hydrolyzed at a different rate. Alternatively, the agent 12 may compose a gel, or other high viscosity fluid operable to effect the desired time release, through shearing due to gravity. More preferably, the gaps 16*a* and planar slats 18 are adjustable, so as to vary the rate of seepage and therefore time release, for example, by pushing down on the apex to cause resistively bendable planar slats 18 to spread radially. Alternatively, the device 10 may further include a manually shiftable outer cover (not shown) that shifts between exposed and closed positions, such that the agent 12 is exposed to the oral cavity 102 and released only when the cover is in the exposed position.

Figure 6:
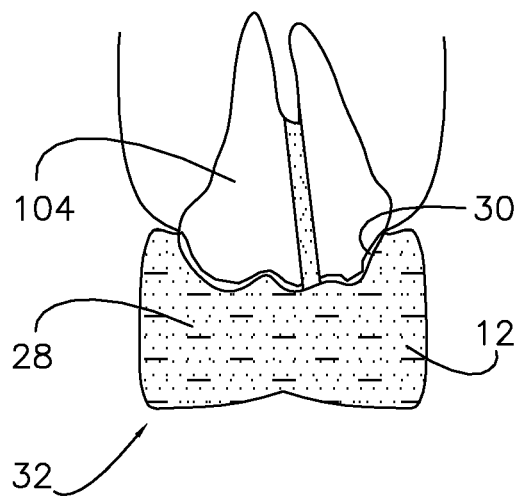
FIG. 6 is an elevation of a temporary crown formed of a polymer matrix impregnated with an anti-biotic agent, wherein the crown is attached to and delivers a medicant to a treated tooth, in accordance with a preferred embodiment of the invention.

In another embodiment, the agent 12 or compound 14 may be coated onto the carrier 16 (FIGS. 3 and 6). More particularly, the device 10 may present a hard coat 22 formed at least in part by agent 12 over-molded upon a solid base 24, wherein the term "coat" is not limited to thin superjacent layers, but includes three-dimensional molds of material. The underlying structure 24 may be of any suitable shape or form, so long as it enables attachment to the tooth 104 and provides enough surface area for receiving the coat 22. In the exemplary configuration shown in FIG. 3, an attachment prong or stem 26 extends from the base 24, and provides increased surface area for retaining the coat 22.

In a third embodiment, the carrier 16 may be formed interstitially by a matrix, honeycomb, or the like, which defines an interconnected labyrinth or plurality of discrete gaps 28 (FIGS. 4, and 4*a-c*). In this configuration, the agent 12 and/or compound 14 is stored within the gaps 28, and gradually released over the period. For example, the carrier 16 may be formed of a polymer matrix, wherein the agent 12 is combined within the polymer as an ingredient prior to fabrication. Once molded and implanted, the agent 12 diffuses from the carrier 16 gradually. In one example, two polymers may be mixed with a macromolecular drug, which diffuses out of the device 10 in a controlled fashion after implantation, gradually escaping through gaps 28 in the polymer matrix over a ninety-day period. It is appreciated that the macromolecular drug is held in place by intermolecular "hydrophobic" interactions that facilitate its slow diffusion through the matrix.

Figure 4:
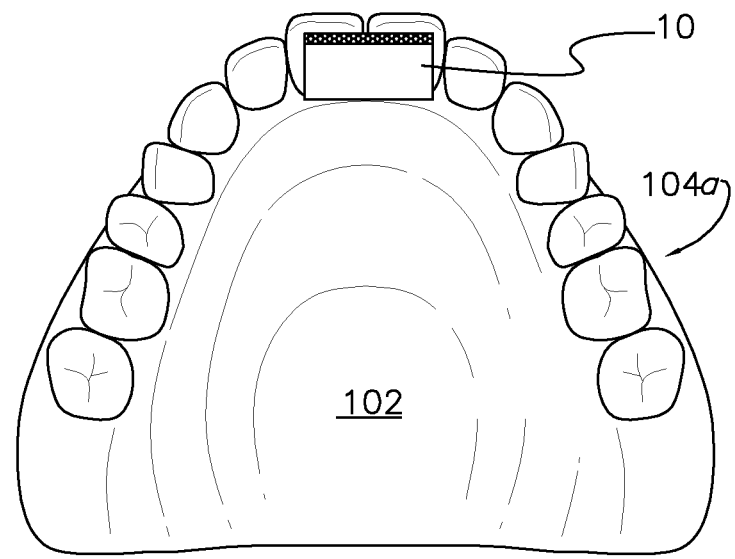
FIG. 4 is a perspective view of an exemplary set of upper teeth, and a pad-type implantation device formed of a dissolvable matrix impregnated with a treating agent and adhered to the interior surface of two adjacent teeth.
Figures 4A, 4B, 4C:
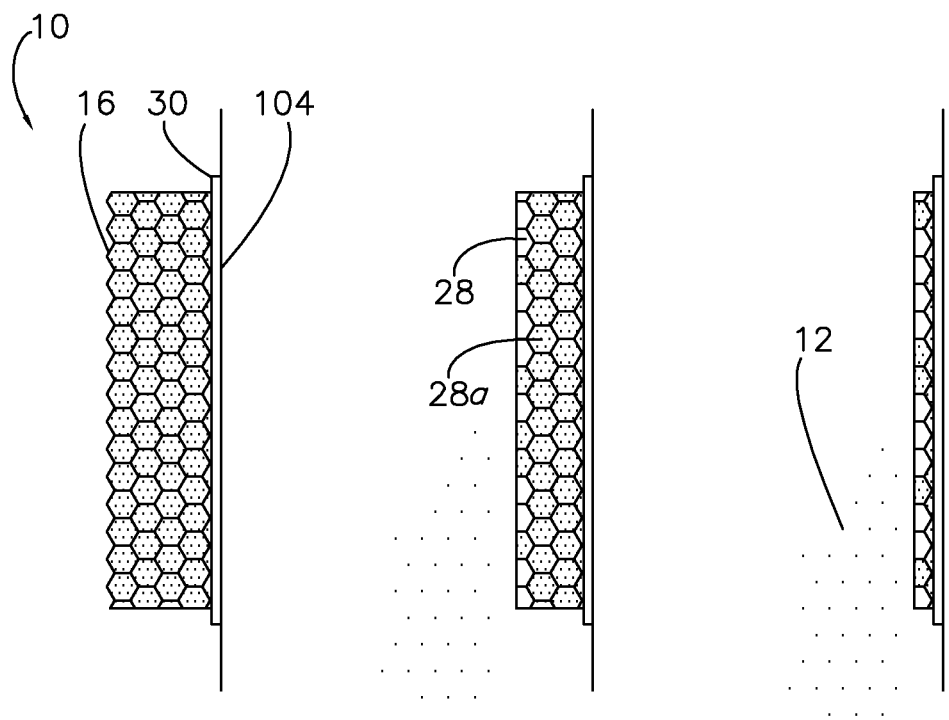
FIG. 4a is a side elevation of a pad-type device defining a plurality of discrete gaps containing treating agent, in accordance with a preferred embodiment of the invention.
FIG. 4b is a side elevation of the device shown in FIG. 4a, partially dissolved, so as to expose internal gaps to the oral cavity.
FIG. 4c is a side elevation of the device shown in FIG. 4a,b, more completely dissolved.

More preferably, the matrix material is also dissolvable over the period, so as to gradually expose the interior gaps 28*a* to the releasing conditions of the cavity 102 (FIGS. 4*a-c*). As a result, the agent 12 stored within the internal gaps 28*a* are incrementally released as layers of the matrix wear off, and may be a conventional liquid or solid that is instantaneously released once exposed. Suitable dissolvable material must be digestible without harm by the user 100, and may include starches and cellulose material.

Especially where the agent 12 presents a prescription strength drug or medicant, the preferred device 10 is intended for implantation (and removal where necessary) by a trained healthcare provider. In a dental setting, for example, the carrier 16 may be bonded to at least one tooth 104 by applying a quantity of a preloaded dental composite material 30 (e.g., a glass ionomer) intermediate the carrier 16 and tooth 104 (FIG. 2), and curing the material 30 with a non-UV light source (not shown). Again, it is appreciated that the hold strength of the material 30 is such that the device 10 does not become dislodged through ordinary usage of the mouth. Thus, a preferred method further includes manually breaking the bond through instrumentation and/or exposing the material 30 to a dissolving agent after use.

It is certainly within the ambit of the present invention, however, for the user 100 to self-apply an over-the-counter device 10, particularly where the agent 12 is aromatic or flavor producing. For example, a pad-type implantation device 10 formed of a dissolvable matrix impregnated with an aromatic and/or flavor producing agent may be adhered to an interior lateral surface 108 of the teeth 104, so as to be adjacent the tongue region best suited to taste the flavor. In FIG. 4, a pad-type device 10 comprising a sweet flavor producing agent is adhered to the interior surface 108 of the user's two front teeth, so as to engage the tip of the user's tongue. Interior disposition of aromatic agents 12 may further offer a discrete solution to halitosis and other mal conditions.

Figure 5:
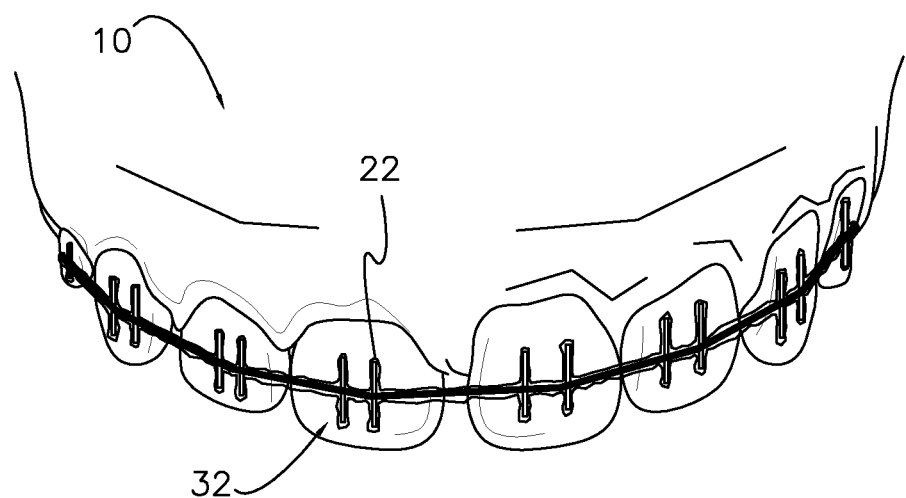
FIG. 5 is a front elevation of an upper set of teeth donning orthodontic braces, wherein the braces have been retrofitted by applying a coat of treating agent to its exterior surface, in accordance with a preferred embodiment of the invention.

As shown in FIGS. 5 and 6, the present invention may be used to retrofit an existing or combined with a new orthodontic device (e.g., a set of braces, dentures, a crown, filling, etc.) 32, so that the orthodontic device 32 is further operable to deliver a time released agent 12 to the user 100. For example, it is appreciated that a coat 22 may be used to retrofit an existing orthodontic device 32, such as a set of braces (FIG. 5); or an orthodontic device 32, such as a crown, may be newly formed of a polymer matrix impregnated by the agent 12 as previously described. In the setting of a temporary crown 32, for example, it is appreciated that an anti-biotic agent 12 may be administered so as to continue the treatment of an infected tooth and/or abscess after a root canal (FIG. 6). To that end, it is appreciated that the crown 32 may present an impervious exterior shell, except where engaging the root canal, so as to direct the medicant 12 thereto. To effect the retrofit prior to placement, an exterior surface of the orthodontic device 32 may be dipped in, sprayed, or otherwise engaged with a liquid compound comprising the agent 12, which hardens to form the coat 22. After placement, the coat 22 may be applied directly to the device 32, and for example, may be brushed on in liquid form, and allowed/caused to cure into a hardened material.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Also, as used herein, the terms "first", "second", and the like do not denote any order or importance, but rather are used to distinguish one element from another, and the terms "the", "a", and "an" do not denote a limitation of quantity, but rather denote the presence of at least one of the referenced item. All ranges directed to the same quantity of a given component or measurement is inclusive of the endpoints and independently combinable.

What is claimed is:

1. A method of orally administering a treating agent to a user over an extended period, wherein the user defines an oral cavity, and presents a plurality of teeth within the cavity and a remainder portion, said method comprising:

affixing a carrier having an internal reservoir to a surface of one or more of the plurality of teeth in the oral cavity of the user, wherein the internal reservoir is defined by a plurality of planar slats emanating from a base and converging at an apex of the carrier, the slats forming a plurality of open gaps between the slats through which fluid can enter and exit the reservoir;

disposing the agent into the internal reservoir of the carrier;

releasing the agent from the carrier over the period within the cavity; and delivering the agent to the remainder portion of the user as a result of releasing the agent over the period.

2. The method as claimed in claim 1, wherein the period is not less than one day.

3. The method as claimed in claim 1, wherein the user further defines a mucous membrane lining within the cavity, and wherein delivering the agent to the remainder portion of the user further includes enabling the agent to be absorbed across the lining.

4. The method as claimed in claim 1, wherein the user generates saliva, the agent is retained by hydrolysable bonds, and wherein the saliva enters the internal reservoir, the agent is exposed to the saliva in the internal reservoir, and the agent is carried from the reservoir by the saliva.

5. The method as claimed in claim 1, wherein the agent is selected from the group consisting essentially of therapeutic agents, medicants, and aromatic/flavor agents.

6. The method as claimed in claim 5, wherein the agent is selected from the group consisting of alkylating, anti-metabolite, analgesic, anti-biotic, and anti-anxiety agents.

7. The method as claimed in claim 6, wherein the agent includes minocycline microspheres.

8. The method as claimed in claim 1, wherein the agent composes a time release compound.

9. The method as claimed in claim 8, wherein the compound further includes an effervescent couple.

10. The method as claimed in claim 8, wherein the cavity generally presents a pH value, and the compound further includes an ingredient operable to adjust the pH within the cavity.

11. The method as claimed in claim 1, wherein affixing the carrier to the surface comprises bonding the carrier to the surface by applying a quantity of a preloaded dental composite material intermediate the carrier and surface and curing the material with a non-UV light source.

12. The method as claimed in claim 1, wherein the carrier includes an insertion hole and wherein disposing the agent into the internal reservoir further comprises:
  disposing the agent through the insertion hole and into the internal reservoir.

13. The method as claimed in claim 1, further comprising:
  adjusting the slats to change the size of the open gaps therebetween and to change the rate at which the agent is released from the reservoir.

14. The method of claim 13, wherein adjusting the slats to change the size of the open gaps further comprises:
  depressing the apex of the carrier toward the base to flex the slats radially outward.

15. The method of claim 1, wherein the carrier includes a cover that shifts between exposed and closed positions, such that the agent is exposed to the oral cavity and released only when the cover is in the exposed position between the slats, and wherein the cover is shifted relative to the slats to change the size of at least one of the open gaps.

* * * * *